United States Patent [19]

Proctor

[11] 4,197,177
[45] Apr. 8, 1980

[54] APPARATUS FOR ANALYSIS OF NITROGEN OXIDES

[76] Inventor: Albert E. Proctor, "Nerhaven", Taplow Common Rd., Burnham, Buckinghamshire, England

[21] Appl. No.: 907,999

[22] Filed: May 22, 1978

[51] Int. Cl.² .............................................. G01N 27/46
[52] U.S. Cl. .............................. 204/195 R; 23/232 E; 204/1 T; 324/425; 422/98
[58] Field of Search .......................... 204/1 N, 195 R; 23/254 E, 232 E; 324/29; 422/98

[56] References Cited

U.S. PATENT DOCUMENTS

| | | | |
|---|---|---|---|
| 3,028,317 | 4/1962 | Wilson et al. | 204/195 R X |
| 3,236,759 | 2/1966 | Robinson | 204/195 R |
| 3,314,863 | 4/1967 | Hersch et al. | 204/1 N |
| 3,835,322 | 9/1974 | Komatsu | 23/232 E X |
| 3,856,473 | 12/1974 | Dillon | 23/254 E |

FOREIGN PATENT DOCUMENTS 1264441  2/1972  United Kingdom .

OTHER PUBLICATIONS

P. Hersch et al., J. Air Pollution Control Assoc., vol. 13, No. 11, pp. 538-541 (1963).
Paul Hersch et al., "Galvanic Monitoring of Nitrogen Dioxide and Nitric Acid", pp. 1-18, (1963).

*Primary Examiner*—G. L. Kaplan
*Attorney, Agent, or Firm*—Fitch, Even & Tabin

[57] ABSTRACT

Apparatus for analyzing the concentration of nitrogen oxides in a gas draws the gas through three separate housings in succession. Moisture is removed from the gas in the first housing and an oxidizing agent in the second chamber converts the nitrogen oxides in the dried gas into nitrogen dioxide. The third housing contains an electrolytic cell producing an electric signal proportional to the concentration of nitrogen dioxide in the converted gas. The electrolytic cell has an anode of activated carbon in a perforated jacket located in a neutral electrolyte and a cathode contacted by the converted gas. The cathode is composed of platinum tape wound onto a support. A sheath of glass fibres contacts both the cathode and the electrolyte and lifts the electrolyte by capillary action to wet the cathode.

13 Claims, 1 Drawing Figure

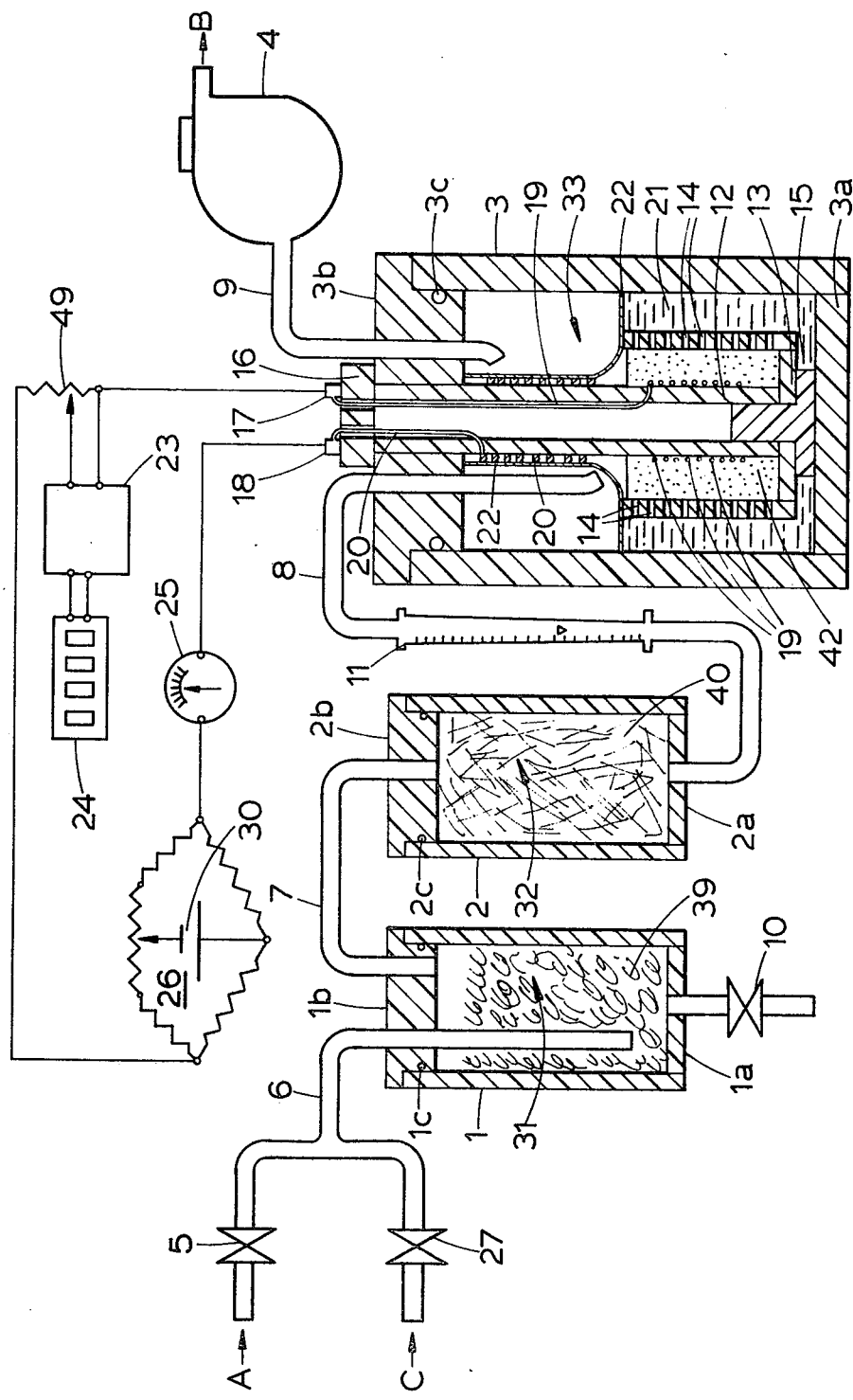

APPARATUS FOR ANALYSIS OF NITROGEN OXIDES

BACKGROUND TO THE INVENTION

The present invention relates to apparatus for use in analysing the concentration of nitrogen oxides in a gas.

Apparatuses for analysing nitrogen oxides in gases or in the atmosphere are known. By way of examples, reference may be made to (a) U.K. Patent Specification 1,264,441, (b) an article entitled "Trace Addition of Nitric Oxide and Nitrogen Dioxide to Air by Electrolysis" by P. Hersch and R. Deuringer published in the Journal of the Air Pollution Control Association November 1963 Volume 13 No. 11 P 538–541 and (c) an article entitled "Instrumental Methods for the detection of Higher Oxides of Nitrogen in Nitrous Oxide" by J. T. Shaw published in the British Journal of Anaesthesia (1968) 40 P. 299–303.

These known forms of apparatus are primarily intended for use in the laboratory and necessitate samples of the gas or atmosphere to be collected and brought to the laboratory for analysis.

Apparatus made in accordance with the invention is especially useful for determining the pollution of air or combustion exhaust in situ. The presence of nitrogen oxides in the atmosphere in excess of 5 parts per million is nowadays regarded as harmful. In this context there is a need for a simple reliable rugged apparatus which can be used in the vicinity of combustion equipment, for example, as opposed to a laboratory. A general object of this invention is to provide apparatus which will satisfy this need.

SUMMARY OF THE INVENTION

In its broadest aspect the invention provides apparatus for use in analysing the concentration of nitrogen oxides in a gas. The apparatus includes means for converting nitrogen oxides in the gas to be analysed into nitrogen dioxide and an electrolytic cell adapted to produce an electrical signal proportional to the concentration of the nitrogen dioxide in the converted gas. The electrolytic cell employs a neutral aqueous electrolyte contained in a sealed chamber. An anode of the cell is composed of activated carbon within a perforated jacket or container immersed in said electrolyte. A cathode of the cell is composed of platinum supported above the electrolyte for direct contact with the converted gas. Means wets the cathode with the electrolyte and establishes electrical contact between the electrolyte and the cathode.

A small battery-powered fan can draw the gas at a controlled flow rate through another sealed chamber containing an oxidizing agent, acting as the conversion means, and then through the chamber containing the electrolytic cell. It is useful to provide a simple flow meter to indicate the gas flow rate.

In many industrial applications the atmosphere containing nitrogen oxides to be analysed is moist and in these cases it is desirable to initially dry the atmosphere prior to conversion. This can be accomplished by a dehydrating agent in a further sealed chamber. The various chambers can be interconnected by pipes or the like.

Conveniently, some or all the various chambers of the apparatus can be defined by housings made from transparent acrylic resin permitting a visual inspection of their contents.

The electrolytic or fuel cell may employ a cathode in the form of platinum foil or tape wound in helical fashion around a tubular support. This support may extend into the perforated jacket and may additionally support platinum wire wound around the support inside the jacket to contact with the carbon therein. Platinum leads or wires may then connect the cathode and the anode to terminals on a cap of a housing defining the sealed chamber of the cell and the leads may be conducted through or alongside the tubular support.

Preferably the electrolyte is buffered and is conducted to the cathode by capillary action. Glass fibres, conveniently woven or otherwise meshed, to form a stable sheath-like structure can serve as the capillary wetting means.

The output from the cell may feed an amplifier driving a recording or indicating means. To permit calibration, it is desirable to include in the measuring circuit, means for backing-off the standing e.m.f., produced by the cell in the presence of pure air.

The invention may be understood more readily and various other features of the invention may become apparent from consideration of the following description.

BRIEF DESCRIPTION OF DRAWINGS

An embodiment of the invention will now be described, by way of example only, with reference to the accompanying drawing which is a schematical representation of apparatus made in accordance with the invention.

DESCRIPTION OF PREFERRED EMBODIMENT

As shown in the drawing, the apparatus has a main inlet A for receiving the gas to be treated and analyzed and an outlet B for discharging the gas after treatment. The gas may be air, or exhaust gas, containing nitrogen oxides and the apparatus is designed to provide an automatic and continuous measurement of the concentration of these nitrogen oxides. The incoming gas is drawn from the inlet A and through various chambers in the apparatus, described hereinafter, by means of a small blower or fan 4 which is driven by a d. c. source in the form of a battery (not shown). The outlet B is here the direct outlet of the fan 4.

The inlet A is connected through a valve 5, which can be selectively opened or closed to a branched conduit or pipe 6 which has a main limb which leads into a first chamber 31 defined by a housing 1. A second conduit or pipe 7 leads from the first chamber 31 to a second chamber 32 defined by a housing 2. A third conduit or pipe 8 leads from the chamber 32 to a third chamber 33 defined by a housing 3. The pipe 8 is provided with a flow meter 11 adapted to directly indicate the flow rate of the gas passing through the apparatus. A fourth conduit or pipe 9 leads from the chamber 33 to the inlet of the fan 4. All the conduits or pipes are preferably made from synthetic plastics.

The housings 1, 2, 3 are conveniently provided with main walls of cylindrical shape. Each housing 1, 2, 3 also has a bottom wall 1a, 2a, 3a, respectively. The bottom wall 1a, 2a, 3a may be formed integrally with or fixed to the main wall or else detachably affixed thereto. Each housing 1, 2, 3 also has a top wall or cover 1b, 2b, 3b respectively which is detachably mounted to the main wall. The covers 1b, 2b, 3b are hermetically sealed to the main wall of the respective housing 1, 2, 3 with the aid of seals in the form of O-rings 1c, 2c, 3c, respectively to seal the chambers 31, 32, 33 from the surroundings. The housings 1, 2, 3 defining the chambers 31, 32, 33 and composed of the main walls, the bottom walls 1a, 2a, 3a, and the covers 1b, 2b, 3b are made from a material, preferably a synthetic material, capable of resisting shock and chemical action. Suitable synthetic materials are various cross-linked polyesters and acrylic resins. A transparent acrylic resin is especially suitable since it additionally permits visual inspection of the contents of the housing.

A further inlet C is connected through a valve 27, which can be selectively opened or closed, to the conduit 6. With the valve 5 closed and the valve 27 opened an inert gas can be passed through the apparatus as a flushing agent. During normal operation when the gas fed to the inlet A is analysed, the valve 5 is opened and the valve 27 is closed.

The first chamber 31 is a dehydration chamber wherein moisture is initially removed from the gas to be analysed. The first chamber 31 contains a suitable dehydrating agent or substance 39, such as calcium chloride, although a mass of small glass spheres or beads is also effective in removing moisture from the gas by condensation. It is possible to provide a suitable cooling means for cooling the chamber 31 thereby to enhance the dehydration process. The liquid formed in the chamber 31 collects on the bottom wall 1a of the housing 1. A drain tube with a valve 10, which can be selectively opened or closed, enables the liquid to be removed from the chamber 31 from time to time.

The second chamber 32 is an oxidation chamber wherein the nitrogen oxides in the dried gas taken from the chamber 31 are converted into nitrogen dioxide ($NO_2$). The second chamber 32 contains material 40 for effecting the conversion of the nitrogen oxides. The material 40 may comprise one or more oxidizing agents such as $CrO_3$, sodium dichromate and potassium permanganate. Conveniently, the oxidizing agent is supported on an inert carrier, such as glass fibres or pumice, although the oxidizing agent may be in the form of fine solid particles.

The third chamber 33 contains a fuel cell or an electrolytic measuring cell designed to react galvanically to the nitrogen dioxide to thereby produce an e.m.f., directly proportional to the $NO_2$ contained in the gas taken from the chamber 32. As shown, the chamber 33 contains a central tubular support 12 fixed at its lower end to a jacket or cup 13 surrounding the lower region of the support 12. The wall of the cup 13 is perforated with a large number of openings 14. The cup 13 and the support 12 are carried by a plug 15 resting on the lower wall 3a of the housing 3. The support 12 extends through the cover 3b of the housing 3 and the interior of the support 12 is closed off with the aid of a cap 16. The support 12 is sealed with respect to the cover 3b and conveniently these parts can be secured together. It is possible to provide a screw-threading or a friction fit between the support 12 and the cover 3b while maintaining the requisite sealing of the chamber 33 from its surroundings. It is preferable to make the support 12, the cup 13 and the cap 16 from the same material as the housing 3, e.g., acrylic resin.

A thin platinum wire 19 is wound in a helical fashion around the lower region of the support 12 within the cup 13. The space between the cup 13 and the support 12 contains activated carbon in the form of activated graphite granules 42 contacting the wire 19. The wire 19 extends through a boring in the wall of the support 12 at the lower region of the latter and passes up through the support 12 to extend through the cap 16 and connect with a terminal 17. The terminal 17 can extend through the cap 16 to contact the wire 19 if preferred. In the illustrated case however the wire 19 is sealed to the cap 16 where it passes through the latter and preferably the wire 19 is also sealed to the support 12 where it passes therethrough to commence the helical configuration.

A thin platinum foil or tape 20 is also wound in a helical fashion around an intermediate region of the support 12 above the cup 13. Similarly to the wire 19 the tape 20 extends through the wall of the support 12 and passes up through the support to connect with a second terminal 18. As with the wire 19, the terminal 18 can extend through the cap 16 or to the cap 16 and the support 12. These measures ensure that the sealing between the chamber 33 and its surroundings is maintained.

A neutral buffered aqueous electrolyte 21 is contained in the space between the cup 13 and the lower part of the chamber 33. A layer of glass fibres 22 conveniently woven together is formed into a sheath extending around the tape 20 on the support 12 and widening out at the bottom to directly contact the electrolyte 21. The glass fibres 22 tend to lift electrolyte by capillary action. Hence, the tape 20 is wetted and maintained in electrical contact with the electrolyte 21 to form the cathode of the measuring cell. The terminal 18 is thus the cathodic terminal. The electrolyte 21 is also in electrical contact with the graphite 42 via the openings 14 in the wall of the cup 13. The graphite 42 forms the anode of the measuring cell which is connected via the wire 19 to the terminal 17 forming the anodic terminal.

The electrolyte 21 may consist of a solution containing 3.0 mols of KCl, 0.1 mols of $K_2HPO_4$ and 0.1 mols of $KH_2PO_4$ per liter.

The gas containing $NO_2$ enters the open region of chamber 33 via the conduit 8 and is led to the moistened platinum cathode. The following galvanic reaction then takes place:

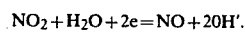

$$NO_2 + H_2O + 2e = NO + 2OH'.$$

The liberated hydroxyl radicals pass through the electrolyte of the measuring cell and are collected at the anode, thus:

$$C + 2O'H' = CO + H_2O + 2e.$$

An e.m.f. proportional to the quantity or concentration of $NO_2$ is thus generated across the terminals 17, 18. This e.m.f. can be measured and/or displayed by any suitable arrangement.

The drawing depicts one arrangement where the terminals 17, 18 are connected to a series measuring circuit composed of a potentiometer 49, a compensating bridge 26 with a d.c. battery 30 and a micro-ammeter 25. An amplifier 23 driven by a voltage developed across the potentiometer feeds a display instrument 24 which conveniently presents a digital display directly indicative of the prevailing quantity of $NO_2$. It is also possible to have a monitoring or recording instrument which produces a curve on recording paper for example, showing the $NO_2$ content over a period of time.

The bridge 26 enables the measuring circuit to be reliably calibrated and set to back-off the standing e.m.f. created by the cell. This calibration is best carried out when pure air, i.e., air free of nitrogen oxides, is passed through the apparatus. In this way the recording instrument can be set to record a zero $NO_2$ content prior to actual operation. It is possible to include one or more temperature-sensitive components in the bridge 26 to automatically compensate for temperature change.

The entire apparatus as described can be mounted in a conveniently-portable protective casing and is independent of mains supply. This enables a user to make measurements of nitrogen oxides in combustion products, for example, in situ. In this way safe reliable monitoring of nitrogen oxides can be carried out. In certain cases adjustment of a combustion process can be effected to achieve maximum thermal efficiency and the apparatus as described can be useful in enabling a suitable compromise between maximum efficiency and the lowest concentration of nitrogen oxides.

I claim:

1. In an apparatus for use in analysing the concentration of nitrogen oxides in a gas; said apparatus including means for converting nitrogen oxides in the gas to be analysed into nitrogen dioxide and an electrolytic cell for producing an electrical signal proportional to the concentration of the nitrogen dioxide in the converted gas; the improvement comprising an electrolytic cell containing a neutral aqueous electrolyte in a sealed chamber; an anode in said sealed chamber comprising activated carbon within a perforated jacket immersed in said electrolyte; a cathode in said sealed chamber comprising a platinum element supported above the electrolyte for direct contact with the converted gas; and capillary means in said sealed chamber extending between said electrolyte and said cathode for wetting the cathode with the electrolyte and for establishing electrical contact between the electrolyte and the cathode.

2. Apparatus according to claim 1 and further comprising means for causing the gas to flow in succession through the converting means and the electrolytic cell.

3. Apparatus according to claim 2, wherein the means for causing the gas to flow is in the form of a battery-powered fan.

4. Apparatus according to claim 1, wherein the cathode is in the form of platinum tape wound in helical fashion around a tubular support, the platinum tape being arranged above the jacket.

5. Apparatus according to claim 4, wherein the support at least extends into the perforated jacket and platinum wire is wound in helical fashion around the support inside the jacket to establish connection with the anodic carbon.

6. Apparatus according to claim 4, wherein said wetting-means comprises a sheath of glass fibres partly surrounding the tubular support.

7. Apparatus according to claim 1, wherein a cylindrical housing with a cap defines the sealed chamber and a pair of terminals are provided on the cap and are connected with the anode and cathode, respectively, with platinum wire.

8. Apparatus according to claim 1 wherein the converting means comprises an oxidizing agent contained in another sealed chamber provided with an ingress and egress for the gas which is converted in said other chamber.

9. Apparatus according to claim 1 and further comprising means for drying the gas prior to conversion.

10. Apparatus according to claim 9, wherein the drying means comprises a dehydrating agent contained in a further sealed chamber.

11. Apparatus according to claim 1, wherein the sealed chamber is defined by a housing which is made from a transparent acrylic resin.

12. Apparatus according to claim 1, and further comprising a flow meter for indicating the flow rate of the gas.

13. Apparatus according to claim 1 and further comprising a measuring circuit with means for indicating or recording the electrical signal produced by the electrolytic cell and calibrating means for backing-off the e.m.f. produced by the cell when pure air is supplied to the cell.

* * * * *